United States Patent
Hagiya et al.

(10) Patent No.: US 6,703,528 B2
(45) Date of Patent: Mar. 9, 2004

(54) PROCESS FOR PRODUCING CARBONYL OR HYDROXY COMPOUND

(75) Inventors: Koji Hagiya, Ibaraki (JP); Naoyuki Takano, Ibaraki (JP); Akio Kurihara, Suita (JP)

(73) Assignee: Sumitomo Chemical Company, Limited, Osaka (JP)

( * ) Notice: Subject to any disclaimer, the term of this patent is extended or adjusted under 35 U.S.C. 154(b) by 28 days.

(21) Appl. No.: 09/925,523

(22) Filed: Aug. 10, 2001

(65) Prior Publication Data

US 2002/0025906 A1 Feb. 28, 2002

(30) Foreign Application Priority Data

| Aug. 11, 2000 | (JP) | 2000-244277 |
| Oct. 27, 2000 | (JP) | 2000-328812 |
| Oct. 27, 2000 | (JP) | 2000-328816 |
| Nov. 6, 2000 | (JP) | 2000-337150 |
| Nov. 6, 2000 | (JP) | 2000-337151 |
| Nov. 6, 2000 | (JP) | 2000-337152 |

(51) Int. Cl.$^7$ .......... C07C 45/00; C07C 31/34; C07C 27/00
(52) U.S. Cl. ....... 568/317; 568/347; 568/349; 568/363; 568/385; 568/391; 568/395; 568/401; 568/467; 568/428; 568/479; 568/568; 568/571; 568/844; 568/850; 568/861; 568/864
(58) Field of Search ............. 568/317, 347, 568/349, 363, 385, 391, 395, 401, 467, 478, 479, 568, 571, 578, 844, 850, 861, 864; 562/523, 527, 534, 535, 546, 547; 423/587, 591

(56) References Cited

U.S. PATENT DOCUMENTS

| 3,972,944 A | 8/1976 | Waldmann et al. |
| 4,532,079 A | 7/1985 | Venturello et al. |
| 4,587,057 A | 5/1986 | Yuasa et al. |
| 4,833,272 A | 5/1989 | Nakazawa et al. |
| 4,859,799 A | 8/1989 | Campestrini et al. |
| 5,047,582 A | 9/1991 | Brotherton et al. |

FOREIGN PATENT DOCUMENTS

| EP | 0 122 804 A1 | 10/1985 |
| GB | 2067550 A | 7/1981 |
| JP | 58121234 | 7/1983 |
| JP | 61275376 | 12/1986 |
| JP | 6236008 | 2/1987 |
| JP | 6346732 | 9/1988 |
| JP | 6356207 | 11/1988 |
| JP | 684324 | 10/1994 |
| JP | 699355 | 12/1994 |
| JP | 761972 | 7/1995 |
| JP | 819027 | 2/1996 |
| JP | 8295649 | 11/1996 |
| JP | 1041485 | 2/1998 |
| JP | 200086574 | 3/2000 |
| JP | 2000159693 | 6/2000 |
| WO | WO9847847 | 10/1998 |

OTHER PUBLICATIONS

Furukawa et al., Chemistry Letters, pp. 877–880, (1988).
Ishii et al., J. Org. Chem., vol. 53, pp. 3587–3593 (1988).
Jingfa et al., Tetrahedron, vol. 48, No. 17, pp. 3503–3514 (1992).
Sato et al., Science, pp. 1646–1647, vol. 281, Sep. 11, 1998.
Deng et al., Green Chemistry, pp. 275–276, Dec. 1999.
Kaneda et al., J. Chem. Soc., Chem. Comm., pp. 1467–1468, (1990).
Oguchi et al., Chemistry Letters, pp. 857–860, (1989).
Antonelli et al., J. Org. Chem., vol. 63, pp. 7190–7206, (1998).
Brooks et al., Chem. Commun., pp. 37–38, (1999).
Venturello et al., Synthesis, pp. 295–297, (1989).
Mugdan et al., J. Chem. Soc., pp. 2988–3000, (1949).
Okamoto et al., Bull Chem. Soc. Japan, pp. 2723–2724, (1989).
Kudo et al., Nature, vol. 312, pp. 537–538, (1984).
Mizuno et al., Bull. Chem. Soc. Jpn., vol. 8, pp. 1066–1072, (1991).
Adam et al., Chem. Ber. 1996, vol. 129, p. 1453–1455, (1996).
Ogata et al., J. Org. Chem., vol. 43, No. 9, p. 1760–1763, (1978).
Mattucci et al., Chemical Communications, p. 1198–1199, (1970).

*Primary Examiner*—Samuel Barts
*Assistant Examiner*—SiKarl A. Witherspoon
(74) *Attorney, Agent, or Firm*—Birch, Stewart, Kolasch & Birch, LLP

(57) ABSTRACT

There are disclosed are a method for producing at least one compound selected from a carbonyl compound and a hydroxy adduct compound by an oxidative cleavage or addition reaction of an olefinic double bond of an olefin compound,
    which contains
        reacting an olefin compound with hydrogen peroxide, utilizing as
    a catalyst, at least one member selected from
        (a) tungsten,
        (b) molybdenum, or
        (c) a tungsten or molybdenum metal compound containing
            (ia) tungsten or (ib) molybdenum and
            (ii) an element of Group IIIb, IVb, Vb or VIb excluding oxygen, and
a catalyst composition.

16 Claims, No Drawings

PROCESS FOR PRODUCING CARBONYL OR HYDROXY COMPOUND

BACKGROUND OF THE INVENTION

1. Field of the Invention

The present invention relates to an oxidation catalyst and methods using the same for producing carbonyl compounds and hydroxy adduct compounds by oxidative cleavage of an olefinic double bond or addition reaction thereto.

A method for producing adipic acid by reacting, in the presence of sodium tungstate and trioctylmethylammonium sulfate, cyclohexene with an aqueous hydrogen peroxide is known (JP-A 2000-86574), and a method for producing an aldehyde by reacting an olefin with hydrogen peroxide, using heteropolyacid containing phosphorus or germanium, is also known (JP-B 6-84324).

However, yields of the desired products in these methods were not always satisfactory for an industrial scale of production.

SUMMARY OF THE INVENTION

According to the present invention, carbonyl compounds and hydroxy adduct compounds can be obtained by using a readily available oxidation catalyst, which can selectively provide desired compounds in an improved yield.

Thus, the present invention provides:

1. a method for producing at least one compound selected from a carbonyl compound and a hydroxy adduct compound by an oxidative cleavage or addition reaction of an olefinic double bond of an olefin compound, which comprises
    reacting an olefin compound with hydrogen peroxide, utilizing as a catalyst, at least one member selected from
    (a) tungsten,
    (b) molybdenum or
    (c) a tungsten or molybdenum metal compound comprising
        (ia) tungsten or (ib) molybdenum and
        (ii) an element of Group IIIb, IVb, Vb or VIb excluding oxygen;

2. an oxidation catalyst composition obtained by reacting aqueous hydrogen peroxide with at least one member selected from
    a tungsten or molybdenum metal compound comprising
        (ia) tungsten or (ib) molybdenum, and
        (ii) an element of Group IIIb, IVb, Vb or VIb excluding oxygen,
provided that said tungsten metal compound is not tungsten carbide;

3. an oxidation catalyst composition obtained by
    reacting aqueous hydrogen peroxide with at least one member selected from
    (a) tungsten,
    (b) molybdenum, or
    (c) a tungsten or molybdenum metal compound comprising
        (ia) tungsten or (ib) molybdenum, and
        (ii) an element of Group IIIb, IVb, Vb or VIb excluding oxygen,
and containing an organic solvent;

4. a method for producing a carbonyl compound of formula (II):

$$R_a R_b C=O \quad (II),$$

wherein a and b respectively represent 1 and 2, or 3 and 4, which comprises subjecting a hydroxy adduct compound of formula (III):

$$X—(R_1)(R_2)C—C(R_3)(R_4)OH \quad (IIIa)$$

wherein X is a hydroperoxide group, and $R_1$ to $R_4$ represent a hydrogen atom or an organic residue, to a decomposition reaction;

5. a method for producing a hydroxy adduct compound of formula (IIIb):

$$X—(R_1)(R_2)C—C(R_3)(R_4)OH \quad (IIIb)$$

wherein X is a hydroxy group and $R_1$ to $R_4$ independently represent a hydrogen atom or an organic residue, which comprises reacting a hydroxy adduct compound of formula (IIIa):

$$X—(R_1)(R_2)C—C(R_3)(R_4)OH \quad (IIIa)$$

wherein X is a hydroperoxide group, and $R_1$ to $R_4$ are the same as defined above, with a reducing agent;

6. a hydroxy adduct compound of formula (III):

$$X—(R_1)(R_2)C—C(R_3)(R_4)OH \quad (III)$$

wherein X is a hydroperoxide group or a hydroxy group, $R_1$ and $R_2$ represent a methyl group, $R_3$ represents a hydrogen atom, and $R_4$ represents a group of formula:

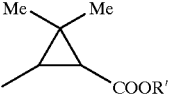

wherein R' is an alkyl, aryl or aralkyl group, and 7. a hydroxy adduct compound of formula (IIIa):

$$X—(R_1)(R_2)C—C(R_3)(R_4)OH \quad (IIIa)$$

wherein X represents a hyroperoxide group, $R_1$ represents a methyl group, $R_3$ represents a hydrogen atom, and $R_2$ and $R_4$ form a group of formula:

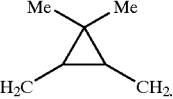

DETAILED DESCRIPTION OF THE INVENTION

First, the method for producing at least one compound selected from a carbonyl compound and a hydroxy adduct compound by an oxidative cleavage or addition reaction of an olefinic double bond of an olefin compound is described.

The method is conducted, for example, by reacting the olefin compound and the metal or the metal compound, which is utilized as a catalyst, with hydrogen peroxide, or it may be conducted in such a manner that the metal or the metal compound is reacted with aqueous hydrogen peroxide to form a catalyst composition and subsequently the olefin compound is reacted with hydrogen peroxide in the presence of the catalyst composition so produced. Thus the production method may be conducted by reacting hydrogen peroxide with the metal or the metal compound, and reacting the olefin compound with hydrogen peroxide, simultaneously in the same reactor, or in the presence of the catalyst composition, The metal or the metal compound is described below.

Examples of the tungsten metal compound comprising tungsten and an element of Group IIIb include tungsten boride and the like. Examples of the tungsten metal compound comprising tungsten and an element of Group IVb include tungsten carbide, tungsten silicide and the like. Examples of the tungsten metal compound comprising tungsten and an element of Group Vb include tungsten nitride, tungsten phosphide, Examples of the tungsten metal compound comprising tungsten and an element of Group VIb other than oxygen include tungsten sulfide and the like. Preferred are tungsten, tungsten boride, tungsten carbide and tungsten sulfide.

Example of the molybdenum metal compound comprising molybdenum and an element of Group IIIb include molybdenum boride, Examples of the molybdenum metal compound comprising molybdenum and an element of Group IVb include molybdenum carbide, molybdenum silicide and the like. Examples of the molybdenum metal compound comprising molybdenum and an element of Group Vb include molybdenum nitride, molybdenum phosphide and the like. Examples of the molybdenum metal compound comprising molybdenum and an element of Group VIb other than oxygen include molybdenum sulfide and the like. Preferred are molybdenum and molybdenum boride.

Any shape of the metal compounds can be used in the present invention. Preferred are those of smaller particle. A catalytic amount of the metal or metal compound may be used in the present production method. A typical amount thereof may be 0.001 to 0.95 mole per mol of the olefin compound.

Hydrogen peroxide is usually used in a form of an aqueous solution. A solution of hydrogen peroxide in an organic solvent may also be used. Any concentration of hydrogen peroxide in an aqueous solution or in an organic solvent solution may be used, and preferred concentration is 1 to 60% by weight. For example, commercially available aqueous hydrogen peroxide may be used without any modification, or, if necessary, it may be used after adjustment of its concentration by dilution, concentration or the like.

The solution of hydrogen peroxide in an organic solvent can be prepared, for example, by such means as extracting of an aqueous hydrogen peroxide solution with an organic solvent or removing water by distillation of the aqueous solution, preferably in the presence of an appropriate organic solvent, which includes such a solvent that may form an azeotrope with water. Examples of the organic solvent include ether type solvents such as diethyl ether, methyl tert-butyl ether, tetrahydrofuran or the like, ester solvents such as ethyl acetate or the like, alcohol solvents such as methanol, ethanol, tert-butanol or the like, and alkylnitrile solvents such as acetonitrile, propionitrile or the like. Any amount of organic solvents may be used, and is typically not more than 100 parts by weight per 1 part by weight of the olefin compound. Preferred organic solvent is an inert organic solvent and is for example, t-butanol or methyl t-butyl ether.

The amount of hydrogen peroxide that may be used is usually not less than 1 mole per mol of the olefin compound. There is no particular upper limit of the amount of hydrogen peroxide that may be used, but a preferred amount thereof is not more than 50 moles per mol of the olefin compound, and a preferred amount thereof may be set for the olefin compound and the desired products therefrom as below.

The oxidation catalyst composition of the present production method can be obtained by reacting aqueous hydrogen peroxide with at least one metal or metal compound as described above to form the catalyst composition as a homogeneous solution or a suspension, both of which can be used. The amount of the hydrogen peroxide is preferably 5 moles or more per mol of the metal or the metal compound. The organic solvent as described above may be used to produce the catalyst composition containing the organic solvent, which may be further dehydrated prior to use, if necessary. Typical examples of the dehydrating agents include anhydrous magnesium sulfate, anhydrous sodium sulfate, anhydrous boric acid, polyphosphoric acid, diphosphorous pentaoxide and the like.

The reacting of the metal or the metal compound with hydrogen peroxide may be conducted at any temperature, and preferably at −10 to 100° C.

In the present production method, the carbonyl compound and the hydroxy adduct compound can be obtained by an oxidative cleavage and addition reaction of an olefinic double bond of an olefin compound.

The carbonyl compound, which results in the oxidative cleavage of the olefin double bond, optionally followed by further oxidation, include ketone, aldehyde, and a carboxylic acid, and the hydroxy adduct compound include diol or (3-hydroxyhydroperoxide compound.

The olefin compound that may be used include an olefin compound of formula (I):

$$R_1R_2C=CR_3R_4 \qquad (I),$$

wherein $R_1$ to $R_4$ are the same or different and represent a hydrogen atom or an organic residue, and two geminal groups or two groups which are in syn position among the $R_1$, $R_2$, $R_3$ and $R_4$ groups may form a divalent organic residue, provided that $R_1$ to $R_4$ do not simultaneously represent a hydrogen atom.

The carbonyl compound that may be produced includes a carbonyl compound of formula (II):

$$R_aR_bC=O \qquad (II),$$

wherein a and b respectively represent 1 and 2, or 3 and 4, or $R_b$ represents a hydroxy group.

The carbonyl compound of formula (II) above include a compound of formula (IV):

$$R_1R_2C=O, \text{ and } R_3R_4C=O \qquad (IV)$$

wherein $R_1$ to $R_4$ are the same as defined above.

The hydroxy adduct compound that may be produced include a compound of formula (III):

$$X-(R_1)(R_2)C-C(R_3)/(R_4)OH \qquad (III),$$

wherein X represents a hydroxy group or a hydroperoxide group.

Substituent groups $R_1$ to $R_4$ are described below.

Examples of the organic residue include alkyl, alkoxy, aryl, aryloxy, aralkyl and aralkyloxy groups, alkylcarbonyl, arylcarbonyl, aralkylcarbonyl, alkoxycarbonyl, aryloxycarbonyl, aralkyloxycarbonyl, carboxyl and carbonyl groups, all of which may be substituted.

The divalent organic residue means a group formed by the above described groups and specific examples thereof include an alkylene, oxaalkylene, arylene, oxaarylene, aralkylene, oxaalkylene, alkylenecarbonyl, arylenecarbonyl, aralkylenecarbonyl, alkyleneoxacarbonyl, arylenoxacarbonyl, aralkylenoxacarbonyl groups or the like, all of which may be substituted.

Preferred organic residue are alkyl, aryl, aralkyl, alkylcarbonyl, arylcarbonyl, aralkylcarbonyl, alkoxycarbonyl, aryloxycarbonyl, aralkyloxycarbonyl, carboxyl and carbonyl groups, all of which may be substituted and corresponding divalent organic residues, which may be substituted.

The alkyl groups in the alkyl, alkoxy, aralkyl, aralkyloxy, alkylcarbonyl, aralkylcarbonyl, alkoxycarbonyl and aralkyloxycarbonyl groups include a linear, branched or cyclic alkyl group having 1 to 20 carbon atoms such as a methyl group, an ethyl group, a n-propyl group, an isopropyl group, a n-butyl group, an isobutyl group, a sec-butyl group, a tert-butyl group, a n-pentyl group, a n-hexyl group, a n-heptyl group, a n-octyl group, a n-nonyl group, a n-decyl group, a cyclopropyl group, a 2,2-dimethylcyclopropyl group, a cyclopentyl group, a cyclohexyl group and a menthyl group.

Examples of the aryl groups in the aryl, aryloxy, aralkyl, aralkyloxy, arylcarbonyl, aralkylcarbonyl, aryloxycarbonyl and aralkyloxycarbonyl groups include a phenyl group, a naphthyl group and the like.

The aralkyl group means a group comprising the ary group and the alkyl group as described above.

The alkoxy, aryoxy and aralkyloxy groups mean groups that respectively comprising corresponding alkyl, aryl and aralkyl groups and an oxy group.

The alkylcarbonyl, arylcarbonyl, aralkylcarbony, alkoxycarbonyl, aryoxycarbonyl, aralkyloxycarbony groups mean groups respectively comprising alkyl, aryl, aralkyl, alkoxy, aryoxy and aralkyloxy groups and a carbonyl group, Examples of the alkyl groups, which may be substituted, for example, include an alkyl group substituted with the alkoxy, aryloxy or aralkyloxy group, the halogen atom, the alkylcarbonyl, arylcarbonyl, alkoxycarbonyl, aryloxycarbonyl, aralkyloxycarbonyl, carboxyl or carbonyl group as described above.

The alkyl moieties of the alkoxy, alkoxycarbonyl, alkylcarbonyl may also be substituted as the alkyl groups described above.

Examples of the halogen atoms include a fluorine atom, a chlorine atom, a bromine atom and the like.

Specific examples of the alkyl groups, which may be substituted include, for example, a chloromethyl group, a fluoromethyl group, a trifluoromethyl group, a methoxymethyl group, an ethoxymethyl group, a methoxyethyl group, a carbomethoxymethyl group and the like.

The aryl groups in the aryl, aryloxy, aralkyl, aralkyloxy, arylcarbonyl, aralkylcarbonyl, aryloxycarbonyl and aralkyloxycarbonyl groups may be substituted with the alkyl, aryl, alkoxy, aralkyl, aryloxy or aralkyloxy group or a halogen atom as described above.

Specific examples of the aryl groups, which may be substituted include, for example, a phenyl group, a naphthyl group, a 2-methylphenyl group, a 4-chlorophenyl group, a 4-methylphenyl group, 4-methoxyphenyl group, a 3-phenoxyphenyl group and the like.

Specific examples of the aryloxy group, which may be substituted include, for example, a phenoxy group, a 2-methylphenoxy group, a 4-chlorophenoxy group, a 4-methylphenoxy group, a 4-methoxyphenoxy group and a 3-phenoxyphenoxy group.

Specific examples of the aralkyl group, which may be substituted include, for example, a benzyl group, a 4-chlorobenzyl group, a 4-methylbenzyl group, a 4-methoxybenzyl group, a 3-phenoxybenzyl group, a 2,3,5,6-tetrafluorobenzyl group, a 2,3,5,6-tetrafluoro-4-methylbenzyl group, a 2,3,5,6-tetrafluoro-4-methoxybenzyl group, a 2,3,5,6-tetrafluoro-4-methoxymethylbenzyl group and the like.

Examples of the alkylcarbonyl, arylcarbonyl, and aralkylcarbonyl groups respectively include, for example, a methylcarbonyl group, an ethylcarbonyl group, a phenylcarbonyl group, a benzylcarbonyl group and the like.

Examples of the alkoxycarbonyl, aryloxycarbonyl and aralkyloxycarbonyl groups respectively include, for example, a methoxycarbonyl group, an ethoxycarbonyl group, a phenoxycarbonyl group, a benzyloxycarbonyl group and the like.

Specific examples of the linear, branched or cyclic alkoxy groups having 1 to 20 carbon atoms include a methoxy group, an ethoxy group, a n-propoxy group, an isopropoxy group, a n-butoxy group, an isobutoxy group, a sec-butoxy group, a tert-butoxy group, a n-pentyloxy group, a n-decyloxy group, a cyclopentyloxy group, a cyclohexyloxy group, a menthyloxy group and the like.

Examples of the alkoxy group, which may be substituted include, for example, a chloromethoxy group, a fluoromethoxy group, a trifluoromethoxy group, a methoxymethoxy group, an ethoxymethoxy group, a methoxyethoxy group and the like.

Specific examples of the aralkyloxy group, which may be substituted include a benzyloxy group, a 4-chlorobenzyloxy group, a 4-methylbenzyloxy group, a 4-methoxybenzyloxy group, a 3-phenoxybenzyloxy group, a 2,3,5,6-tetrafluorobenzyloxy group, a 2,3,5,6-tetrafluoro-4-methylbenzyloxy group, a 2,3,5,6-tetrafluoro-4-methoxybenzyloxy group, a 2,3,5,6-tetrafluoro-4-methoxymethylbenzyloxy group and the like.

Examples of the olefin of formula (I) wherein three of the $R_1$ to $R_4$ groups represent a hydrogen atom, which are referred to as "mono-substituted olefin" include 1-hexene, 1-heptene, 1-octene, 1-undecene, styrene, 1,7-octadiene and allyl benzyl ether. Further examples of the olefin compound, which are referred to as "di-substituted terminal olefin", include 2-methylpropene, 2-methyl-4,4-dimethyl-1-propene, 2-ethyl-1-butene, 2-methyl-1-pentene, α-methylstyrene, α-phenylstyrene, methylenecyclobutane, methylenecyclopentane, methylenecyclohexane, β-pinene, camphene, 1,3,3-trimethyl-2-methylindorine and α-methylene-γ-butyrolactone.

Examples of the olefin of formula (I) wherein two groups of $R_1$ to $R_4$ groups represent a hydrogen atom, which are referred to as "di-substituted internal olefin, include cyclopentene, cyclohexene, cycloheptene, cyclooctene, 3-methylcyclopentene, 4-methylcyclopentene, 3,4-dimethylcyclopentene, 3,5-dimethylcyclopentene, 3,4,5-trimethylcyclopentene, 3-chlorocyclopentene, 3-methylcyclohexene, 4-methylcyclohexene, 3,4-dimethylcyclohexene, 3,5-dimethylcyclohexene, 3,4,5-trimethylcyclohexene, 2-hexene, 3-hexene, 5-dodecene, norbomene, phenanthrene, 1,2,3,4-tetrahydrophthalic anhydride, dicyclopentadiene, indene, methyl 3,3-dimethyl-2-(1-propenyl)-cyclopropanecarboxylate, ethyl 3,3-dimethyl-2-(1-propenyl)-cyclopropanecarboxylate and the like.

Examples of the olefin compound of formula (I) wherein one of the $R_1$ to $R_4$ groups represents a hydrogen atom, which are referred to as "tri-substituted oletin", include 2-methyl-2-pentene, 3-methyl-2-pentene, 3-ethyl-2-pentene, 2-methyl-2-hexene, 3-methyl-2-hexene, 2-methyl-1-phenylpropene, 2-phenyl-2-butene, 1-methylcyclopentene, 1,3-dimethylcyclopentene, 1,4-dimethylcyclopentene, 1,5-dimethylcyclopentene, 1,3,5-trimethylcyclopentene, 1,3,4-trimethylcyclopentene, 1,4,5-trimethylcyclopentene, 1,3,4,5-tetramethylcyclopentene, 1-methylcyclohexene, 1,3-dimethylcyclohexene, 1,4-dimethylcyclohexene, 1,5-dimethylcyclohexene, 1,3,5-trimethylcyclohexene, 1,3,4-trimethylcyclohexene, 1,4,5-trimethylcyclohexene, 1,3,4,5-tetramethylcyclohexene, isophorone, 2-carene, 3-carene, α-pinene, methyl 3,3-dimethyl-2-(2-methyl-1-propenyl)-cyclopropanecarboxylate, ethyl 3,3-dimethyl-2-(2-methyl-1-propenyl)-cyclopropanecarboxylate, isopropyl 3,3-dimethyl-2-(2-methyl-1-propenyl)-cyclopropanecarboxylate, tert-butyl 3,3-dimethyl-2-(2-methyl-1-propenyl)-cyclopropanecarboxylate, cyclohexyl 3,3-dimethyl-2-(2-methyl-1-propenyl)-cyclopropanecarboxylate, Menthyl 3,3-dimethyl-2-(2-methyl-1-propenyl)-cyclopropanecarboxylate, benzyl 3,3-dimethyl-2-(2-methyl-1-propenyl)-cyclopropanecarboxylate, (4-chlorobenzyl) 3,3-dimethyl-2-(2-methyl-1-propenyl)-cyclopropanecarboxylate, (2,3,5,6-tetrafluorobenzyl) 3,3-dimethyl-2-(2-methyl-1-propenyl)-cyclopropanecarboxylate, (2,3,5,6-tetrafluoro-4-methylbenzyl) 3,3-dimethyl-2-(2-methyl-1-propenyl)-cyclopropanecarboxylate, (2,3,5,6-tetrafluro-4-methoxybenzyl) 3,3-dimethyl-2-(2-methyl-1-propenyl)-cyclopropanecarboxylate, (2,3,5,6-tetrafluoro-4-methoxymethylbenzyl) 3,3-dimethyl-2-(2-methyl-1-propenyl)-cyclopropanecarboxylate, (3-phenoxybenzyl) 3,3-dimethyl-2-(2-methyl-1-propenyl)-cyclopropanecarboxylate and the like.

Examples of the olefin compound of formula (I) wherein $R_1$ to $R_4$ groups do not represent a hydrogen atom, which are referred to as "tetra-substituted olefin", include 2,3-dimethyl-2-butene, 1,2-dimethylcyclopenteen, 1,2-dimethylcyclohexene, 1,2,3,4,5,6,7,8-octahydronaphthalene, 1-isopropylidene-2-carboethoxy-3-methylcyclopentane, cyclohexylidenecyclohexane, tetraphenylethylene, 2,3-dimethyl-4-methoxyindene, 2,3-di(4-acetoxyphenyl)-2-butene, pulegone and the like.

The reaction of the olefin compound with hydrogen peroxide is typically conducted at a temperature range of from 0 to 200° C. and the reaction temperature may be preferably set as below within the range in view of the olefin compound and the desired products of the reaction.

For example, the carbonyl compound of formula (IV) wherein $R_1$ to $R_4$ represent an organic residue can be produced, as a major product, by reacting the olefin compound of formula (I) with hydrogen peroxide preferably in the presence of an organic solvent and a dehydrating agent and at 30 to 100° C., wherein the amount of hydrogen peroxide is preferably 2 to 10 moles per mol of the olefin compound.

The carbonyl compound of formula (IV) wherein at least one of $R_1$ to $R_4$ groups represents a hydrogen atom, can be produced, as a major product, by reacting the olefin compound of formula (I) with hydrogen peroxide preferably in the presence of an organic solvent and a dehydrating agent and at 30 to 65° C., wherein the amount of hydrogen peroxide is preferably 2 to 10 moles per mol of the olefin compound.

The carbonyl compound of formula (II) wherein $R_b$ represents a hydroxy group, can be produced, as a major product, by reacting the olefin compound of formula (1) wherein at least one group of $R_1$ to $R_4$ represents a hydrogen atom, with aqueous hydrogen peroxide preferably at 65 to 100° C., wherein the amount of hydrogen peroxide is preferably 4 moles or more per mol of the olefin compound.

The method of the present invention may also be carried out in the presence of a boron compound such as boric anhydride, Examples of the boron compound include boric anhydride, metaboric acid, orthoboric acid, alkali metal salts of metaboric acid, alkaline earth metal salts of metaboric acid, alkali metal salts of orthoboric acid and alkaline earth metal salts of orthoboric acid. Any amount of such a compound may be used, but it usually not more than 1 mole per mol of the olefin compound.

The hydroxy adduct compound of formula (IIIb):

$$X-(R_1)(R_2)C-C(R_3)(R_4)OH \qquad (IIIb),$$

wherein X represents a hydroxy group and R1 to R4 represent the same as defined above, can be produced, as a major product, preferably by reacting the olefin of formula (I) with aqueous hydrogen peroxide at 0 to 65° C., wherein the amount of aqueous hydrogen peroxide is preferably 1 to 2 moles per mol of the olefin compound.

The β-hydroxyhydroperoxide compound of formula (III) wherein X represents a hydroperoxide group, can be produced, as a major product, preferably in the presence of an organic solvent and a dehydrating agent at 0 to 45° C., wherein the amount of hydrogen peroxide is preferably 2 to 10 moles per mol of the olefin compound.

Examples of the dehydrating agent include, for example, anhydrous magnesium sulfate, sodium sulfate. The amount of such a dehydrating agent that may be used is not particularly limited, and preferably such an amount of the dehydrating agent that can absorb, as crystal water, water that may be present in an aqueous hydrogen peroxide solution.

Next the olefin compound of formula (I) is described.

Examples of the olefin compound include, for example, a mono-substituted olefin such as 1-hexene or a di-substituted internal olefin such as cyclohexene, the carbon-carbon double bond in the olefin is cleaved by oxidation to yield an aldehyde and a carboxylic acid.

Further examples of the olefin compound include, for example, di-substituted terminal olefins such as methylenecyclohexane and the like, and the carbon-carbon double bond in the olefin is cleaved by oxidation to yield ketone. Yet further examples of the olefin compound include, for example, tri-substituted olefins such as 2-methyl-2-pentene and the like, which is reacted to yield a ketone, an aldehyde and a carboxylic acid by oxidative cleavage of the carbon-carbon double bond. Moreover, examples of the olefin compound include tetra-substituted olefins such as 2,3-dimethyl-2-butene or the like, which is oxidized to yield ketone.

The progress of the reaction can be checked by conventional analyzing means such as gas chromatography, high performance liquid chromatography, thin layer chromatography, NMR and IR.

After completion of the reaction, the desired compound can be separated by subjecting the reaction solution as-obtained or that resulting after decomposition of the remaining hydrogen peroxide with a reducing agent such as sodium sulfite, to concentration, crystallization or the like. Moreover, the resulting compounds can also be separated by adding, if necessary, water and/or a water-immiscible organic solvent to the reaction mixture, then extracting and subsequently concentrating the resulting organic layer. The desired compound separated may further be purified by such a means as distillation and/or column chromatography.

Examples of the water-immiscible organic solvent include aromatic hydrocarbon solvents such as toluene and xylene, halogenated hydrocarbon solvents such as dichloromethane, chloroform and chlorobenzene, ether solvents such as diethyl ether, methyl tert-butyl ether and tetrahydrofuran and ester solvents such as ethyl acetate. The amount of such solvents that may be used is not particularly limited.

The filtrate resulting from the separation of the desired compound by crystallization and the separated aqueous layer resulting from the extraction of the reaction solution that contain the present catalyst composition used in the reaction and can be reused as a recovered catalyst composition, directly or after being subjected to some treatment such as concentration if required, in the reaction according to the present invention.

The carboxylic acid produced may be further decarboxylated in the reaction system, to give, for example, a carboxylic acid having one less carbon atoms such as the case of isophorone.

Furthermore, when optical isomers are used as the organic compound, an optically active product can be obtained according to the position of the asymmetric carbon.

The β-hydroxyhydroperoxide of formula (III) obtained in the present method can be further derivatized to carbonyl compound of formula (IV):

$$R_1R_2C=O, \text{ and } R_3R_4C=O$$

wherein $R_1$ to $R_4$ independently represent a hydrogen atom or an organic residue. The reaction process comprises decomposing a hydroxy adduct compound of formula (IIIa):

$$X-(R_1)(R_2)C-C(R_3)(R_4)OH \qquad (IIIa)$$

wherein X is a hyroperoxide group, and $R_1$ to $R_4$ are the same as defined above.

The decomposition reaction is conducted by contacting the hydroxy adduct compound with a catalyst selected from a metal compound comprising an element of Group Va, VIII, Ib, IIb, IIIb, IVb, Vb or lanthanide or by heating.

Examples of the metal compound comprising an element of Group Va include vanadium metal, vanadium oxide, vanadium chloride, vanadium carbide, ammonium vanadate, an composition obtained by reacting aqueous hydrogen peroxide with vanadium, niobium, niobium chloride, niobium oxide, niobium ethoxide.

Examples of the metal compound comprising an element of Group VIIa include rhenium metal, rhenium carbonyl, rhenium chloride.

Examples of the metal compound comprising an element of Group VIII include iron metal, iron carbonyl, iron chloride, iron acetylacetonate, ruthenium, ruthenium carbonyl, ruthenium acetylacetonate, ruthenium chloride, tris(triphenylphosphine)ruthenium chloride, cobalt metal, cobalt acetate, cobalt bromide, rhodium metal, rhodium acetate, rhodium carbonyl, iridium metal, iridium chloride, nickel metal, nickel acetylacetonate, palladium metal, palladium acetate, palladium on activated carbon.

Examples of the metal compound comprising an element of Group Ib include copper metal, copper bromide, copper chloride, copper acetate.

Examples of the metal compound comprising an element of Group IIb include zinc metal, zinc chloride.

Examples of the metal compound comprising an element of Group IIb include boron trichloride, boron trifluoride, aluminum metal, aluminum chloride.

Examples of the metal compound comprising an element of Group IVb include tin metal, tin chloride.

Examples of the metal compound comprising an element of Group Vb include bismuth metal, bismuth chloride, antimony metal, antimony bromide.

Examples of the metal compound comprising an element of lanthanide include dysprosium metal, dysprosium chloride.

Preferred are vanadium compound, copper compound, ruthenium compound, palladium compound and mixture of them.

The amount of the catalyst for the decomposition reaction is usually 0.001 to 0.95 mole per mol of the β-hydroxyhydroperoxide. The reaction temperature is usually −20 to 100° C.

The reaction is preferably conducted in the presence of an organic solvent that can dissolve the peroxide. Examples of the organic solvent include the ether solvent, alcohol solvent, alkylnitrile solvent as described above.

Alternatively, a hydroxy adduct compound of formula (IIIb):

$$X-(R_1)(R_2)C-C(R_3)(R_4)OH \qquad (IIIb)$$

wherein X is a hyroxy group and $R_1$ to $R_4$ independently represent a hydrogen atom or an organic residue can be produced by a process, which comprises reacting a hydroxy adduct compound of formula (IIIa):

$$X-(R_1)(R_2)C-C(R_3)(R_4)OH \qquad (IIIa)$$

wherein X is a hyroperoxide group, and $R_1$ to $R_4$ are the same as defined above, with a reducing agent.

Examples of the reducing agent include an inorganic salt having reducing activity such as sodium thiosulfate and an organic compound having reducing activity such as dimethylsulfide, triphenylphosphine and the like.

The reduction reaction is usually carried out at −10 to 100° C/ in an organic solvent. Examples of the organic solvent include those described above for the decomposition reaction of the hydroxy adduct compound (III).

Typical examples of the hydroxy adduct compounds include a hydroxy adduct compound of formula (III):

$$X-(R_1)(R_2)C-C(R_3)(R_4)OH \qquad (III)$$

wherein X is a hyroperoxide group or a hydroxy group, $R_1$ and $R_2$ represent a methyl group, $R_3$ represents a hydrogen atom, and $R_4$ represents a group of formula:

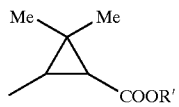

wherein R' represents an alkyl, aryl, or aralkyl group; and a hydroxy adduct compound of formula (III):

$$X-(R_1)(R_2)C-C(R_3)(R_4)OH \qquad (III)$$

wherein X is a hyroperoxide group, $R_1$ represents a methyl group, $R_3$ represents a hydrogen atom, and $R_2$ and $R_4$ form a group of formula:

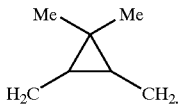

The alkyl, aralkyl or aryl group represented by R' in the above described compounds respectively means the same group as defined for $R_1$ to $R_4$ above.

In the above-described reduction or decomposition reaction of the β-hydroxyhydroperoxide, the reaction mixture or solution after completion of the reaction can be treated in a similar manner to separate the desired product.

Examples of the ketone that is obtained in such a manner include acetone, methyl ethyl ketone, diethyl ketone, methyl propyl ketone, acetophenone, cyclobutanone, cyclopentanone, cyclohexanone, camphenlione, norpinene, 1,3,3-trimethylindorinone, dihydro-2,3-furandione, benzophenone, 2,6-hexanedione, 2,7-octanedione, 1,6-cyclodecanedione, 4-acetoxyacetophenone, 2-methoxy-6-(propan-2-one)acetophenone, 2-carboethoxy-3-methylcyclopentanone, 4-methyl-1,2-cyclohexanedione and the like.

Examples of the aldehyde include formaldehyde, acetaldehyde, propionaldehyde, butylaldehyde, pentylaldehyde, hexylaldehyde, heptylaldehyde, decylaldehyde, undecanylaldehyde, benzaldehyde, 5-oxohexylaldehyde, 2-methyl-5-oxohexylaldehyde, 4-methyl-5-oxohexylaldehyde, 3-methyl-5-oxohexylaldehyde, 2,4-dimethyl-5-oxohexylaldehyde, 3,4-dimethyl-5-oxchexylaldehyde, 2,3-dimethyl-5-oxohexylaldehyde, 2,3,4-trimethyl-5-oxohexylaldehyde, 6-oxoheptylaldehyde, 2-methyl-6-oxoheptylaldehyde, 4-methyl-6oxoheptylaldehyde, 2,4-dimethyl-6-oxoheptylaldehyde, 2,3-dimethyl-6-oxoheptylaldehyde, 3,4-dimethyl-6-oxoheptylaldehyde, 2,3,4-trimethyl-6-oxoheptylaldehyde, glutaraldehyde, adipoaldehyde, heptanedialdehyde, octanedialdehyde, 2-chloroglutaraldehyde, 2-methylglutaraldehyde, 3-methylglutaraldehyde, 2,3-dimethylglutaraldehyde, 2,4-dimethyliglutaraldehyde, 2,3,4-trimethylglutaraldehyde, 2-methyladipoaldehyde, 3-methyladipoaldehyde, 2,3-dimethyladipoaldehyde, 2,4-dimethyladipoaldehyde, 2,3,4-dimethyladipoaldebyde, cyclopentane-1,3-dicarboaldehyde, diphenyl-2,2'-dicarboaldehyde, 1-(formylmethyl)cyclopentene-2,3,4-tricarboaldehyde, 1,2-bis(formyl methyl)succinic anhydride, 1,4-diformylbutane-2,3-dicarboxylic acid, (2-formylmethyl)benzaldehyde, 2,2-dimethyl-3-(2-oxopropyl)cyclopropaneacetaldehyde, 2,2-dimethyl-3-(3-oxobutyl)cyclopropylaldehyde, 2,2-dimethyl-3-(2oxoethyl)cyclobutaneacetaldehyde, methyl 3,3-dimethyl-2-formylcyclopropanecarboxylate, ethyl 3,3-dimethyl-2-formylcyclopropanecarboxylate, isopropyl 3,3-dimethyl-2-formylcyclopropanecarboxylate, tert-butyl 3,3-dimethyl-2-formylcyclopropanecarboxylate, cyclohexyl 3,3-dimethyl-2-formylcyclopropanecarboxylate, menthyl 3,3-dimethyl-2formylcyclopropanecarboxylate, benzyl 3,3-dimethyl-2-formylcyclopropanecarboxylate, (4-chlorobenzyl) 3,3-dimethyl-2-formylcyclopropanecarboxylate, (2,3,5,6-tetrafluorobenzyl) 3,3-dimethyl-2-formylcyclopropanecarboxylate, (2,3,5,6-tetrafluoro-4-methylbenzyl) 3,3-dimethyl-2-formylcyclopropanecarboxylate, (2,3,5,6-tetrafluoro-4-methoxybenzyl) 3,3-dimethyl-2-formylcyclopropanecarboxylate, (2,3,5,6-tetrafluoro-4-methoxymethylbenzyl) 3,3-dimethyl-2-formylcyclopropanecarboxylate and (3-phenoxybenzyl) 3,3-dimethyl-2-formylcyclopropanecarboxylate.

Examples of the carboxylic acid include acetic acid, propionic acid, butanoic acid, pentanoic acid, hexanoic acid, 6-oxoheptanoic acid, 2-methyl-6-oxoheptanoic acid, 3-methyl-6-oxoheptanoic acid, 4-methyl-6-oxoheptanoic acid, 5-methyl-6-oxoheptanoic acid, 2,3-dimethyl-6-oxoheptanoic acid, 2,4-dimethyl-6-oxoheptanoic acid, 3,4-dimethyl-6-oxoheptanoic acid, 2,3,4-trimethyl-6-oxoheptanoic acid, 5-oxohexanoic acid, 2-methyl-5-oxohexanoic acid, 3-methyl-5-oxohexanoic acid, 4- methyl-5-oxohexanoic acid, 2,3-dimethyl-5-oxohexanoic acid, 2,4-dimethyl-5-oxohexanoic acid, 3,4-dimethyl-5-oxohexanoic acid, 2,3,4-trimethyl-5-oxohexanoic acid, 3,3-dimethyl-5-oxohexanoic acid, heptanoic acid, glutaric acid, adipic acid, pimelic acid, suberic acid, 2-methylglutaric acid, 3-methylglutaric acid, 3-chloroglutaric acid, 2,3-dimethylglutaric acid, 2,4-dimethylglutaric acid, 2-methyladipic acid, 3-methyladipic acid, 2,3-dimethyladipic acid, 2,4-dimethyladipic acid, 3,4-dimethyladipic acid, 2,3,4-trimethylglutaric acid, cyclopentane-1,3-dicarboxylic acid, biphenyl-2,2'-dicarboxylic acid, meso-1,2,3,4-tetracarboxylic acid, benzoic acid, 1-(carboxymethyl)cyclopentane-2,3,4-tricarboxylic acid, homophthalic acid, benzyloxyacetic acid, 3-(3-oxobutyl)-2,2-dimethylcyclopropanecarboxylic acid, 3-(2-oxopropyl)-2,2-dimethyl-1-carboxymethylcyclopropane, 3-(2-oxoethyl)-2,2-dimethyl-1-carboxymethylcyclobutane, methyl 3,3-dimethyl-2-carboxycyclopropanecarboxylate, ethyl 3,3-dimethyl-2-carboxycyclopropanecarboxylate, isopropyl 3,3-dimethyl-2-carboxycyclopropanecarboxylate, tert-butyl 3,3-dimethyl-2-carboxycyclopropanecarboxylate, cyclohexyl 3,3-dimethyl-2-carboxycyclopropanecarboxylate, menthyl 3,3-dimethyl-2-carboxycyclopropanecarboxylate, benzyl 3,3-dimethyl-2-carboxycyclopropanecarboxylate, (4-chlorobenzyl) 3,3-dimethyl-2-carboxycyclopropanecarboxylate, (2,3,5,6-tetrafluorobenzyl) 3,3-dimethyl-2-carboxycyclopropanecarboxylate, (2,3,5,6-tetrafluoro-4-methylbenzyl) 3,3-dimethyl-2-carboxycyclopropanecarboxylate, (2,3,5,6-tetrafluoro-4-methoxybenzyl) 3,3-dimethyl-2-carboxycyclopropanecarboxylate, (2,3,5,6-tetrafluoro-4-methoxymethylbenzyl) 3,3-dimethyl-2-carboxycyclopropanecarboxylate, (3-phenoxybenzyl) 3,3-dimethyl-2-carboxycyclopropanecarboxylate and the like.

EXAMPLES

The present invention is further described in detail below with reference to examples, but the invention is not limited to these examples. Gas chromatography method (hereinafter referred to as GC method.

Column: DB-1 (Length : 30 m, i.d.: 0.25 mm, Film thickness:1.0 μm)

Oven temperature: Initial temp.: 100° C. (0 min)→Rate :2° C./min→Second temp.: 180° C. (0 min)→Rate :10° C./min→Final temp.: 300° C.(10 min) Run tine: 62 min Injection temp: 250° C., Detection temp: 250° C.

Carrier gas: He, constant flow 1.0 ml/min

Injection vol.: 1.0 μl, Split ratio : ⅒

Liquid chromatography method(herein after referred to as LC method)

Column: Sumnipax ODS-A212(Length: 15 cm, i.d. :6 mm,5.0 μm)

Carrier: A 0.1 vol % trifluoroacetic acid/water B 0.1 vol % trifluoroacetic acid/acetonitrile Initial A/B=90/10 (volume ratio) (0 min)→after 40 min A/B10/90 (volume ratio) (20 min), flow:1.0 ml/min Injection vol.: 10 μl, Detector: 220 nm,

Example 1

Two grams of a 30 wt % aqueous hydrogen peroxide solution and 97 mg of metallic tungsten were charged into a 50 mL flask equipped with a magnetic rotor and a reflux condenser. The mixture was heated to an inner temperature of 60° C. and then was stirred and maintained at the temperature for 0.5 hour. To the mixture, 3.5 g of isophorone and 25.8 g of a 30 wt % aqueous hydrogen peroxide solution were added dropwise over 20 minutes. After completion of the addition, the reaction solution was heated and stirred for 6 hours on an oil bath inner temperature of which was 95° C. After completion of the reaction, the mixture was cooled to an inner temperature of 25° C. and was analyzed by gas chromatography. The analysis confirmed that 3,3-dimethyl-5-oxohexanoic acid (areal percentage of chromatogram: 55%) was formed.

Example 2

Two grams of a 30 wt % aqueous hydrogen peroxide solution and 30 mg of metallic tungsten were charged into a 50 mL flask equipped with a magnetic rotor and a reflux condenser. The mixture was heated to an inner temperature of 60° C. and then stirred and maintained at the temperature for 0.5 hour. To the resulting mixture, 3.0 g of methyl 3,3-dimethyl-2-(2-methyl-1-propenyl) cyclopropanecarboxylate and 7.3 g of a 30 wt % aqueous hydrogen peroxide solution were charged. After the charge, the reaction solution was heated and stirred for 6 hours on an oil bath inner temperature of which was 95° C. After completion of the reaction, the mixture was cooled to an inner temperature of 25° C. and was analyzed by an internal standard method by gas chromatography. The analysis confirmed that 3,3-dimethyl-2-carbomethoxycyclopropanecarboxylic acid (areal percentage: 43%) was formed.

Example 3

Two grams of a 30 wt % aqueous hydrogen peroxide solution and 90 mg of metallic tungsten were charged into a 50 mL flask equipped with a magnetic rotor and a reflux condenser. The mixture was heated to an inner temperature of 60° C. and then was stirred and maintained at the temperature for 0.5 hour. To the mixture, 4.7 g of 1-methylcyclohexene and 25.6 g of a 30 wt % aqueous hydrogen peroxide solution were added. The reaction solution was thereafter heated and stirred for 10 hours on an oil bath inner temperature of which was 95° C. After completion of the reaction, the mixture was cooled to an inner temperature of 25° C. and was analyzed by an internal standard method by gas chromatography. The analysis confirmed that 6-oxohexanoic acid (yield: 92%) was formed.

Example 4

Into a 50 mL flask equipped with a magnetic rotor and a reflux condenser, 200 mg of a 30 wt % aqueous hydrogen peroxide solution and 40 mg of tungsten boride were added. The mixture was heated to an inner temperature of 40° C. and then was stirred and maintained at the temperature for 0.5 hour. After cooling of this solution to an inner temperature of 25° C., 530 mg of anhydrous magnesium sulfate, 530 mg of a 30 wt % aqueous hydrogen peroxide solution and 1.5 g of tert-butanol were added and then stirred and maintained at the temperature for 1 hour. Thereafter a mixed solution comprising 350 mg of 3carene and 1.5 g of tert-butanol was added dropwise over 10 minutes. The mixture was stirred and maintained at an inner temperature of 25° C. for 24 hours, to this solution 10 g of toluene and 5 g of water was added, and separated to give 9.4 g of the toluene solution. Gas chromatography analysis (an internal standard method) and a liquid chromatography analysis of this reaction solution confirmed that the yield of 4-hydroxy-3-hydroperoxycarene was 70.4% and the yield of 3,4-carenediol 21.7%.

The liquid chromatographys' elution time of 4-hydroxy-3-hydroperoxycarene is 20.9 min. and the mass spectrum showed M+186.

Into a 50 mL flask equipped with a magnetic rotor and a reflux condenser, 200 mg of a 30 wt % aqueous hydrogen peroxide solution and 20 mg of vanadium metal were charged. The mixture was stirred and maintained at the temperature for 0.5 hour. After cooling this solution to an inner temperature of 25° C., the toluene solution of 4-hydroxy-3-hydroperoxycarene was added and then was stirred and maintained at that temperature for 16 hour and then was heated to an inner temperature of 60° C. and then further stirred and maintained at the temperature for 3 hour. Gas chromatography analysis (an internal standard method) and a liquid chromatography analysis of this reaction solution confirmed that the yield of 2,2,-dimethyl-3-(2-oxopropyl)cyclopropane acetaldehyde was 71.4% (in terms of used 3carene).

Example 5

Into a 50 mL flask equipped with a magnetic rotor and a reflux condenser, 200 mg of a 30 wt % aqueous hydrogen peroxide solution, 0.8 g of tert-butanol and 22 mg of tungsten boride were charged. The mixture was heated to an inner temperature of 60° C. and then was stirred and maintained at the temperature for 1 hour, After cooling this solution to 25° C., 530 mg of anhydrous magnesium sulfate was added and thereafter a mixed solution comprising 270 mg of 1-methylcyclohexene, 1.0 g of tert-butanol and 500 mg of a 30 wt % aqueous hydrogen peroxide solution was added dropwise over 20 minutes. After the addition, the mixture was stirred and maintained at an inner temperature of 25° C. for 20 hours. Analysis of the reaction solution by gas chromatography confirmed that 6-oxoheptylaldehyde (area percentage: 77.0%) was formed.

Example 6

Into a 50 mL flask equipped with a magnetic rotor and a reflux condenser, 3 g of tert-butanol, 600 mg of a 30 wt % aqueous hydrogen peroxide solution, 2.3 g of magnesium sulfate, 300 mg of boric anhydride and 40 mg of tungsten boride were charged. The mixture was heated to an inner temperature of 600C and then was stirred and maintained at the temperature for 1 hour. After cooling to an inner temperature of 6° C., a mixed solution comprising 400 mg of methyl trans-3,3-dimethyl-2-(2-methyl-1-propenyl) cyclopropanecarboxylate, 600 mg of a 30 wt % aqueous hydrogen peroxide solution and 1.8 g of tert-butanol was added dropwise over 20 minutes. The mixture was stirred and maintained at an inner temperature of 60° C. for 4 days, to give a reaction solution containing methyl trans-3,3-dimethyl-(1-hydroxy-2-hydroperoxy-2-methylpropyl)

cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropanecarboxylate was 55% and the yield of methyl trans-3,3-dimethyl-2-formylcyclopropanecarboxylate was 5%.

Example 7

Into a 50 mL flask equipped with a magnetic rotor and a reflux condenser, 200 mg of a 30 wt % aqueous hydrogen peroxide solution and 45 mg of tungsten boride were charged. The mixture was heated to an inner temperature of 40° C. and then was stirred and maintained at that temperature for 1 hour. After cooling this solution to an inner temperature of 20° C., 530 mg of anhydrous magnesium sulfate, 400 mg of a 30 wt % aqueous hydrogen peroxide solution and 1.5 g of tert-butanol was added and then stirred and maintained at the temperature for 2 hour. Thereafter a mixed solution comprising 400 mg of methyl trans-3,3-dimethyl-2-(2-methyl-1-propenyl)cyclopropanecarboxylate, and 0.8 g of tert-butanol was added dropwise over 20 minutes. The mixture was stirred and maintained at an inner temperature of 25° C. for 16 hours, to give a reaction solution containing methyl trans-3,3-dimethyl-(1-hydroxy-2-hydroperoxy-2-methylpropyl)cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropanecarboxylate was 60.8% and the yield of methyl trans-3,3-dimethyl-2-formylcyclopropanecarboxylate was 6%.

Example 8

Into a 50 mL flask, 3 g of tert-butanol, 200 mg of a 30 wt % aqueous hydrogen peroxide solution, 16 mg of boric anhydride and 40 mg of metallic tungsten (powder) were charged. The mixture was heated to an inner temperature of 60° C. and then was stirred and maintained at the temperature for 1 hour. After the cooling this solution to an inner temperature of 25° C., 530 mg of magnesium sulfate was added and thereafter a mixed solution comprising 400 mg of methyl trans-3,3-dimethyl-2-(2-methyl-1-propenyl)cyclopropanecarboxylate, 600 mg of a 30 wt % aqueous hydrogen peroxide solution and 1.8 g of tert-butanol was added dropwise over 20 minutes. The mixture was stirred and maintained at an inner temperature of 25° C. for 16 hours, to give a reaction solution containing methyl trans-3,3-dimethyl-(1-hydroxy-2-hydroperoxy-2-methylpropyl)-cyclopropanecarboxylate and methyl trans-3,3-dimethyl-2-formylcyclopropanecarboxylate. Gas chromatography analysis (an internal standard method) and liquid chromatography analysis of this reaction solution confirmed that the yield of trans-3,3-dimethyl-(1-hydroxy-2-hydroperoxy-2-methylpropyl)cyclopropanecarboxylate was 54.8% and the yield of methyl trans-3,3-dimethyl-2-formylcyclopropanecarboxylate was 6%

Example 9

Into a 100 mL flask, 10 g of tert-butanol, 2.0 g of a 30 wt % aqueous hydrogen peroxide solution and 215 mg of tungsten boride were charged. The mixture was heated to an inner temperature of 60° C. and then was stirred and maintained at that temperature for 1 hour. After cooling to an inner temperature of 20° C., a mixed solution comprising 4 g of methyl trans-3,3-dimethyl-2-(2-methyl-1-propenyl) cyclopropanecarboxylate, 4 g of a 30 wt % aqueous hydrogen peroxide solution and 10 g of tert-butanol was dropped over 20 minutes. The mixture was stirred and maintained at an inner temperature of 20° C. for 48 hours, to give a reaction solution containing methyl trans-3,3-dimethyl-(1-hydroxy-2-hydroperoxy-2-methylpropyl) cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropane-carboxlate was 36% and the yield of methyl trans-3,3-dimethyl-2-formylcyclopropanecarboxylate was 4%

Example 10

Into a 50 mL flask, 3 g of tert-butanol, 200 mg of a 30 wt % aqueous hydrogen peroxide solution and 40 mg of metallic tungsten (powder) were charged. The mixture was heated to an inner temperature of 60° C. and then was stirred and maintained at the temperature for 1 hour. After cooling to an inner temperature of 25° C., a mixed solution comprising 400 mg of methyl trans-3,3-dimethyl-2-(2-methyl-1-propenyl)cyclopropanecarboxylate, 400 mg of a 30 wt % aqueous hydrogen peroxide solution and 1.8 g of tert-butanol was added dropwise over 20 minutes. The mixture was stirred and maintained at an inner temperature of 25° C. for 24 hours, to give a reaction solution containing methyl trans-3,3-dimethyl-(1-hydroxy-2-hydroperoxy-2-methylpropyl)cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methypropyl)cyclopropanecarboxylate was 45% and the yield of methyl trans-3,3-dimethyl-2-formylcyclopropanecarboxylate was 5%

Example 11

Into a 50 mL flask, 3 g of methyl tert-butyl ether, 1.2 g of a 30 wt % aqueous hydrogen peroxide solution and 40 mg of tungsten boride were charged. The mixture was heated to an inner temperature of 50° C. and then was stirred and maintained at the temperature for 1 hour. Subsequently, 2.3 g of magnesium sulfate was added and thereafter a mixed solution comprising 400 mg of methyl trans-3,3-dimethyl-2-(2-methyl-1-propenyl)cyclopropanecarboxylate and 1.8 g of methyl tert-butyl ether was added dropwise over 20 minutes. The mixture was stirred and maintained at an inner temperature of 50° C. for 2 hours, to give a reaction solution containing methyl trans-3,3-dimethyl-( 1-hydroxy-2-hydroperoxy-2-methylpropyl)cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropanecarboxylate was 37% and the yield of methyl trans-3,3-dimethyl-2-formylcyclopropanecarboxylate was 4%

Example 12

Into a 50 mL flask, 3 g of tert-butanol, 2.3 g of magnesium sulfate, 300 mg of boric anhydride and 40 mg of tungsten boride were charged. After heating to an inner temperature of 60° C., a mixed solution comprising 400 mg of methyl trans-3,3-dimethyl-2-(2-methyl-1-propenyl) cyclopropanecarboxylate, 600 mg of a 30 wt % aqueous hydrogen peroxide solution and 1.8 g of tert-butanol was added dropwise over 20 minutes and the resulting mixture was stirred and maintained at an inner temperature of 60° C. for 2 hours, to give a reaction solution containing methyl trans-3,3-dimethyl-(1-hydroxy-2-hydroperoxy-2-methylpropyl)cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropanecarboxylate was 42.2% and the yield of methyl trans-3,3-dimethyl-2-formylcyclopropanecarboxylate was 5%

Example 13

Into a 50 mL flask, 3 g of tert-butanol and 51 mg of tungsten sulfide were charged. After heating to an inner temperature of 60° C., a mixed solution comprising 400 mg of methyl trans-3,3-dimethyl-2-(2-methyl-1-propenyl) cyclopropanecarboxylate, 1.5 g of a 30 wt % aqueous hydrogen peroxide solution and 1.8 g of tert-butanol was dropped over 20 minutes and the resulting mixture was stirred and maintained at an inner temperature of 60° C. for 2 hours, to give a reaction solution containing methyl trans-3,3-dimethyl-2-formylcyclopropanecarboxylate. Gas chromatography analysis of this reaction solution confirmed that the areal percentage of methyl trans-3,3-dimethyl-2-formylcyclopropanecarboxylate was 23.8%.

Example 14

A reaction solution containing methyl trans-3,3-dimethyl-2-formylcyclopropanecarboxylate was obtained through operations conducted as in Example 13 except that 50 mg of tungsten silicide was used in place of 51 mg of tungsten sulfide. Gas chromatography analysis of this reaction solution confirmed that the areal percentage of methyl trans-3,3-dimethyl-2-formylcyclopropanecarboxylate was 29.8%.

Example 15

A reaction solution containing methyl trans-3,3-dimethyl-2-formylcyclopropanecarboxylate was obtained through operations conducted in the same manner as Example 13 except that 41 mg of tungsten carbide was used in place of 51 mg of tungsten sulfide. Gas chromatography analysis of this reaction solution confirmed that the areal percentage of methyl trans-3,3-dimethyl-2-formylcyclopropanecarboxylate was 27.7%.

Example 16

Into a 50 mL flask 20 mg of metallic molybdenum (powder) was charged and then 200 mg of a 30 wt % aqueous hydrogen peroxide solution was added, followed by the addition of 530 mg of magnesium sulfate. Furthermore, a mixed solution comprising 400 mg of methyl trans-3,3-dimethyl-2-(2-methyl-1-propenyl) cyclopropanecarboxylate, 600 mg of a 30 wt % aqueous hydrogen peroxide solution and 1.5 g of tert-butanol was added dropwise over 20 minutes and the resulting mixture was stirred and maintained at an inner temperature of 25° C. for 40 hours, to give a reaction solution containing methyl trans-3,3-dimethyl-(1-hydroxy-2-hydroperoxy-2-methylpropyl)cyclopropanecarboxylate and methyl trans-3,3-dimethyl-2-formylcyclopropanecarboxylate. Gas chromatography analysis (an internal standard method) and a liquid chromatography analysis of this reaction solution confirmed that the yield of trans-3,3-dimethyl-(1-hydroxy-2-hydroperoxy-2-methylpropyl)cyclopropanecarboxylate was 51.7% and the yield of methyl trans-3,3-dimethyl-2-formylcyclopropanecarboxylate was 5%. The analysis also revealed that 18.2% (GC areal percentage) of the starting methyl trans-3,3-dimethyl-2-(2-methyl-1-propenyl) cyclopropanecarboxylate remained.

Example 17

A reaction solution containing methyl trans-3,3-dimethyl-2-formylcyclopropanecarboxylate was obtained in a similar manner as in Example 16 except that the amount of the metallic molybdenum (powder) and the reaction time were changed to 40 mg and 20 hours, respectively. Gas chromatography analysis (an internal standard method) of this reaction solution confirmed that the yield was 62.7%. The analysis also revealed that 6% (GC areal percentage) of the starting methyl trans-3,3-dimethyl-2-(2-methyl-1-propenyl) cyclopropanecarboxylate remained.

Example 18

A reaction solution containing methyl trans-3,3-dimethyl-2-formylcyclopropanecarboxylate was obtained in a similar manner as in Example 16 except that 22 mg of molybdenum boride was used in place of 20 mg of metallic molybdenum. Gas chromatography analysis (an internal standard method) and a liquid chromatography analysis of this reaction solution confirmed that the yield of trans-3,3-dimethyl-(1-hydroxy-2-hydroperoxy-2-methylpropyl) cyclopropanecarboxylate was 36.5% and the yield of methyl trans-3,3-dimethyl-2-formylcyclopropanecarboxylate was 4% The analysis also revealed that 20% (GC areal percentage) of the starting methyl trans-3,3-dimethyl-2-(2-methyl-1-propenyl)cyclopropanecarboxylate remained.

Example 19

A reaction solution containing methyl trans-3,3-dimethyl-2-formylcyclopropanecarboxylate was obtained in a similar manner as in Example 16 except that methyl tert-butyl ether was used in place of tert-butanol. Gas chromatography analysis (an Internal standard method) and a liquid chromatography analysis of this reaction solution confirmed that the yield of trans-3,3-dimethyl-(1-hydroxy-2-hydroperoxy-2-methylpropyl)cyclopropanecarboxylate was 47.2% and the yield of methyl trans-3,3-dimethyl-2-formylcyclopropanecarboxylate was 5% The analysis also revealed that 20% (GC areal percentage) of the starting methyl trans-3,3-dimethyl-2-(2-methyl-1-propenyl) cyclopropanecarboxylate remained.

Example 20

Twenty grams of a 30 wt % aqueous hydrogen peroxide solution and 895 mg of metallic tungsten powder were charged into a 1 L flask equipped with an induction stirrer and a reflux condenser and the inner temperature was elevated to 60° C. After heating and maintaining of the mixture at the temperature for 0.5 hour, 40 g of cyclohexene and 228 g of a 30 wt % aqueous hydrogen peroxide solution were added dropwise over 20 minutes. After completion of the dropping, the reaction solution was heated and stirred for 8 hours on an oil bath inner temperature of which was 100°

C. The inner temperature of the reaction solution was elevated from 72° C. to 95° C. After completion of the reaction, the mixture was cooled to an inner temperature of 5° C., and the crystals formed were separated by filtration and dried, to give 57.3 g of white crystals. The analysis of the crystals with 1 H-NMR confirmed that they were adipic acid of high purity. The measurement of the melting point of the crystals confirmed the melting point was 151 to 152° C. The analysis of the filtrate by gas chromatography (the internal standard method) showed that the filtrate contained 9.6 g of adipic acid. The total yield of adipic acid resulting from the separated crystals of adipic acid and the adipic acid in the filtrate was 94%.

Example 21

The filtrate obtained in Example 20 was concentrated to 188 g. The concentrated filtrate was charged into a 1 L flask equipped with an induction stirrer and a reflux condenser, and 40 g of cyclohexene and 250 g of a 30 wt % aqueous hydrogen peroxide solution were added dropwise over 20 minutes. After the dropping, the mixture was heated and stirred for 9 hours on an oil bath inner temperature of which was 100° C. The inner temperature of the reaction solution was elevated from 72° C. to 95° C. After completion of the reaction, the mixture was cooled to an inner temperature of 0° C., and the crystals formed were separated by filtration and dried, to give 57.2 g of white crystals of adipic acid. Melting point: 151 to 152° C. The filtrate was concentrated to 130 g and cooled to an inner temperature of 0° C. The crystals formed were separated by filtration and dried, to give 5.0 g of white crystals of adipic acid. Melting point: 151 to 152° C. The yield of the crystals of adipic acid obtained was 87.5%.

Example 22

Into a 1 L flask equipped with an induction stirrer and a reflux condenser, 122 g of the filtrate obtained in Example 21 was charged, and then 40 g of cyclohexene and 250 g of a 30 wt % aqueous hydrogen peroxide solution were further dropped over 20 minutes. After the addition, the mixture was heated and stirred for 11.5 hours on an oil bath inner temperature of which was 100° C. The inner temperature of the reaction solution was elevated from 72° C. to 95° C. After completion of the reaction, the mixture was cooled to an inner temperature of 0° C., and the crystals formed were separated by filtration and dried, to give 57.5 g of white crystals of adipic acid. Melting point: 151 to 152° C. The filtrate was concentrated to 128 g and cooled to an inner temperature of 0° C. The crystals formed were further separated by filtration and dried, to give 5.2 g of white crystals of adipic acid. Melting point: 151 to 152° C. The yield of the crystals of adipic acid obtained was 88.2%.

Example 23

Into a 1 L flask equipped with an induction stirrer and a reflux condenser, 103 g of the filtrate obtained in Example 22 was charged, and then 40 g of cyclohexene and 250 g of a 30 wt % aqueous hydrogen peroxide solution were further added dropwise over 20 minutes. After the addition, the mixture was heated and stirred for 10.5 hours on an oil bath inner temperature of which was 100° C. The inner temperature of the reaction solution was elevated from 72° C. to 95° C. After completion of the reaction, the mixture was cooled to an inner temperature of 0° C., and the crystals formed were separated by filtration and dried, to give 55.7 g of white crystals of adipic acid. Melting point: 151 to 152° C. The analysis of the filtrate by gas chromatography (internal standard method) showed that the filtrate contained 11.6 g of adipic acid. The yield of adipic acid was 88.9% except the adipic acid contained in 103 g of the filtrate obtained in Example 22.

Example 24

Into a 50 mL flask equipped with a magnetic rotor and a reflux condenser, 2 g of a 30 wt % aqueous hydrogen peroxide solution and 97 mg of metallic tungsten powder were charged and heated to an inner temperature of 60° C. After the heating and maintaining of the mixture at the temperature for 0.5 hour, 4 g of cyclohexene and 25.8 g of a 30 wt % aqueous hydrogen peroxide solution were added dropwise over 20 minutes. After the addition, the mixture was heated and stirred for 6 hours on an oil bath inner temperature of which was 100° C. The inner temperature of the reaction solution was elevated from 72° C. to 95° C. After completion of the reaction, the mixture was cooled to an inner temperature of 5° C., and the crystals formed were separated by filtration and dried, to give 5.3 g of white crystals. The analysis of the crystals with 1H-NMR confirmed that they were adipic acid of high purity. The analysis of the filtrate by gas chromatography (an internal standard method) showed that the filtrate contained 1.4 g of adipic acid. The total yield of adipic acid was 94%.

Example 25

Through the operations conducted in a similar manner as those in Example 24 except that 96 mg of tungsten carbide was used in place of 97 mg of the metallic tungsten powder, 4.5 g of crystals of adipic acid were obtained. The filtrate contained 1.2 g of adipic acid. The total yield of adipic acid was 80%.

Example 26

Through the operations conducted in a similar manner as those in Example 24 except that 96 mg of tungsten boride was used in place of 97 mg of the metallic tungsten powder, 3.6 g of crystals of adipic acid were obtained. The yield of adipic acid: 51%.

Example 27

Through the operations conducted in a similar manner as those in Example 24 except that 121 mg of tungsten sulfide was used in place of 97 mg of the metallic tungsten powder, 5.0 g of crystals of adipic acid were obtained. The filtrate contained 1.12 g of adipic acid. The total yield of adipic acid: 86%.

Example 28

Through the operations conducted in a similar manner as those in Example 24 except that 3.2 g of cyclopentene was used in place of 4 g of cyclohexene, 4.2 g of crystals of glutaric acid were obtained. The filtrate contained 0.93 g of glutaric acid. The total yield of adipic acid resulting from the combination of the separated crystals of glutaric acid and the glutaric acid in the filtrate was 80%.

Example 29

Into a 50 mL flask equipped with a magnetic rotor and a reflux condenser, 0.5 g of a 30 wt % aqueous hydrogen peroxide solution and 37 mg of metallic tungsten were charged. The mixture was heated to an inner temperature of 60° C. and then was stirred and maintained at the temperature for 0.5 hour. To the mixture were charged 2.0 g of 1-heptene and 7.5 g of a 50 wt % aqueous hydrogen peroxide solution. After that, the reaction solution was heated and stirred for 20 hours on an oil bath the inner temperature of which was 95° C. After completion of the reaction, the reaction solution was cooled to an inner temperature of 25° C. and analyzed by gas chromatography (an internal standard method). The analysis showed that 1.2 g of hexanoic acid was formed. Yield. 49%.

Example 30

Into a 50 mL flask equipped with a magnetic rotor and a reflux condenser, 2 g of a 30 wt % aqueous hydrogen peroxide solution and 70 mg of metallic tungsten were charged. The mixture was heated to an inner temperature of 60° C. and then stirred and maintained at that temperature for 0.5 hour. To the mixture were charged 4 g of styrene and 15 g of a 40 wt % aqueous hydrogen peroxide solution. The mixture was heated and stirred for 30 hours on an oil bath the inner temperature of which was 95° C. After completion of the reaction, the reaction solution was cooled to an inner temperature of 25° C., to give 4.3 g of white crystals of benzoic acid. An analysis by gas chromatography confirmed that the purity of the crystals obtained was 98% (areal percentage).

Example 31

Into a 50 mL flask equipped with a magnetic rotor and a reflux condenser, 200 mg of a 30 wt % aqueous hydrogen peroxide solution, 1.5 g of tert-butanol and 40 mg of metallic tungsten powder were charged. The mixture was heated to an inner temperature of 60° C. and then was stirred and maintained at the temperature for 1 hour. After cooling of this solution to an inner temperature of 25° C., 530 mg of anhydrous magnesium sulfate was added and then a mixed solution comprising 150 mg of cyclopentene, 1.5 g of tert-butanol and 350 mg of a 30 wt % aqueous hydrogen peroxide solution was added dropwise over 20 minutes. After stirring and maintaining the mixture at an inner temperature of 25° C. for 16 hours, gas chromatography analysis (an internal standard method) and a liquid chromatography analysis of this reaction solution confirmed that the yield of 1-hydroxy-2-hydroperoxy-cyclopentane was 80.7%. Almost no by-production of the diol compound was recognized.

Example 32

Into a 50 mL flask equipped with a magnetic rotor and a reflux condenser, 200 mg of a 30 wt % aqueous hydrogen peroxide solution, 1.5 g of tert-butanol, 20 mg of boric anhydride and 40 mg of metallic tungsten powder were charged. The mixture was heated to an inner temperature of 60° C. and then was stirred and maintained at that temperature for 1 hour. After cooling of this solution to an inner temperature of 25° C., 530 mg of anhydrous magnesium sulfate was added and then a mixed solution comprising 180 mg of cyclohexene, 1.5 g of tert-butanol and 350 mg of a 30 wt % aqueous hydrogen peroxide solution was added dropwise over 20 minutes. After stirring and maintaining the mixture at an inner temperature of 25° C. for 16 hours, gas chromatography analysis (an internal standard method) and a liquid chromatography analysis of this reaction solution confirmed that the yield of 1-hydroxy-2-hydroperoxy-cyclohexane was 54.7%.

Example 33

Through the operations conducted in a similar manner as those in Example 32 except that 220 mg of 1-heptene was used in place of 180 mg of cyclohexene and that the mixture was stirred and maintained at an inner temperature of 25° C. for 48 hours, 55 mg of hexylaldehyde was obtained. Yield: 25%.

Example 34

Through the operations conducted in a similar manner as those in Example 32 except that 230 mg of styrene was used in place of 180 mg of cyclohexene and that the mixture was stirred and maintained at an inner temperature of 60° C. for 6 hours, 47 mg of benzaldehyde was obtained. Yield: 20%.

Example 35

Through the operations conducted in a similar manner as those in Example 32 except that 370 mg of 5-dodecene was used in place of 180 mg of cyclohexene, that 22 mg of tungsten boride was used in place of 40 mg of metallic tungsten powder and that the mixture was stirred and maintained at an inner temperature of 25° C. for 39 hours, 112 mg of heptylaldehyde (yield: 44%) and pentylaldehyde (yield: 44%) were obtained.

Example 36

Into a 50 mL flask equipped with a magnetic rotor and a reflux condenser, 200 mg of a 30 wt % aqueous hydrogen peroxide solution, 40 mg of metallic tungsten powder and 15 mg of boric anhydride and were charged and the mixture was heated to an inner temperature of 60° C. After stirring and maintaining at the temperature for 0.5 hour, the mixture was cooled to an inner temperature of 25° C. After addition of 1.5 g of tert-butanol and 530 mg of anhydrous magnesium sulfate, a mixed solution comprising 230 mg of 2,3-dimethyl-2-butene, 1.5 g of tert-butanol and 350 mg of a 30 wt % aqueous hydrogen peroxide solution was added dropwise over 20 minutes. After completion of the addition, the mixture was stirred and maintained at an inner temperature of 25° C. for 20 hours. Analysis of the reaction solution by gas chromatography confirmed formation of 243 mg of acetone. The yield was 77% of the theoretical value.

Example 37

Into a 50 mL flask equipped with a magnetic rotor and a reflux condenser, 200 mg of a 30 wt % aqueous hydrogen peroxide solution, 1.5 g of tert-butanol, 16 mg of boric anhydride and 40 mg of metallic tungsten powder were charged and the mixture was heated to an inner temperature of 60° C. After stirring and maintaining at the temperature for 1 hour, 530 mg of anhydrous magnesium sulfate was added and thereafter a mixed solution containing 247 mg of 2,4,4-trimethyl-1-pentene, 1.5 g of tert-butanol and 350 mg of a 30 wt % aqueous hydrogen peroxide solution was added dropwise over 20 minutes. After the addition, the mixture was stirred and maintained at an inner temperature of 60° C. for 6 hours. Analysis of the reaction solution by gas chromatography confirmed the formation of 4,4-dimethylpentane-2-one (areal percentage in the gas chromatogram: 51.0%). The by-production of an epoxy compound was also recognized (areal percentage in the gas chromatography analysis: 25.0%).

Example 38

To a 100 mL flask equipped with magnetic rotor and a reflux condenser were added 4.2 g of metallic tungsten boride powder, 259 of water, and 18 grams of a 60 wt % aqueous hydrogen peroxide solution were added thereto under stirring at 40° C. over 2 hours. The mixture was kept at 40° C. for 2 hours to yield a clear solution with a slight white crystals floating on the surface of the solution. After the solution was cooled to room temperature and hydrogen peroxide was decomposed with platinum net, the solution was evaporated to remove water at room temperature to give white crystals, which was dried at room temperature under open air until the weight thereof became constant. 6.4 g of solid crystal was finally obtained.

UV Absorbtion of the solution (before concentration) $\lambda^{H2O}$max: 200, 235(s) nm.

IR max (solution before concentration) (4000~750 cm$^{-1}$) 3350, 2836, 1275, 1158, 965, 836 cm$^{-1}$ IR max (KBr) (Solid crystal): 3527, 3220, 2360, 2261, 1622, 1469, 1196, 973, 904.5, 884, 791, 640, 549 cm$^{-1}$ Elemental Analysis (found): W: 51.2, 0: 39.0, H: 2.2, B: 3.98

Example 39

A pale yellow clear solution was obtained in a similar manner as described in Example 38 except that 12 g of water was used and 5.4 g of tungsten sulfide was used in place of tungsten boride. A 10.1 g of a pale yellow solid was obtained after drying.

UV Absorbtion of the solution before concentration: $\lambda^{H2O}_{max}$: 200, 240 (s) nm IR (aqueous solution before concentration)

$\lambda_{max}$ (aqueous solution) (4000~750 cm$^{-1}$) :3373, 1187, 1044, 974, 878, 837 cm$^{-1}$ IR (Solid), $\lambda_{max}$ (KBr) ; 3435, 3359, 1730, 1632, 1320, 1285, 1178, 1103, 1070, 1008, 981, 887, 839, 851, 660, 615, 578 cm$^{-1}$ Elemental Analysis(found): W: 35.3, 0: 47.4, H:3.0, S:12.4.

A yellowish solution was obtained in a similar manner as described in Example 38 except that 12 g of water was used and 2.3 g of molybdenum boride was used in place of tungsten boride and 12 g of 60% hydrogen peroxide was used.

UV Absorbtion of the solution before concentration: $\lambda^{H2O}_{max}$: 200, 310 (s) nm IR (Solid), $\lambda_{max}$ (KBr) 3221, 2520, 2361, 2262, 1620, 1463, 1439, 1195, 965, 927, 887, 840, 799, 674, 634, 547, 529 cm$^{-1}$ Elemental Analysis (found): Mo: 35.5, O: 51.0, H: 2.9, B: 4.1

Example 40

To a 50 mL flask equipped with magnetic rotor and a reflux condenser were added 80 mg of metallic tungsten powder, and 400 mg of a 30 wt % aqueous hydrogen peroxide solution were added and reacted under stirring for 0.5 hour. The mixture was cooled to 25° C., and 2 g of t-butanol and 800 mg of 30 wt % hydrogen peroxide were added thereto and stirred for 1 hour. To this solution was added dropwise a mixed solution of 2.0 g of t-butanol and 600 mg of 3-carene over 10 minutes and reacted for 24 hours under stirring at 25° C. The resulting solution was subjected to a reduction reaction by using 27 g of 5wt % of sodium thiosulfate and analyzed by GC to find that 3,4-carene-diol was produced in 70.0% yield.

Example 41

Into a 500 mL flask equipped with a magnetic rotor and a reflux condenser and charged with 1.9 of tungsten metal powder and 7.5 g of water were added dropwise 7.5 g of a 60 wt % aqueous hydrogen peroxide solution at 60° C. over 1 hour under stirring. The resulting reaction mixture was reacted under stirring at the same temperature for 1 hour to give a clear solution. The solution was cooled to room temperature and 38 g of t-butanol and 13.3 g of anhydrous magnesium sulfate were added thereto and stirred for 14 hours at room temperature. To the obtained slurry solution was dropwise added a mixed solution of 10 g of methyl trans-3,3-dimethyl-2-(2-methyl-1-propenyl) cyclopropanecarboxylate and 12 g t-butanol over 20 minutes and reacted at 25 ° C. for 24 hours. 60 g of water was added to the reaction mixture and extracted twice with 50 g of toluene to give 137.4 g of toluene solution.

The toluene solution was analyzed by LC to show that methyl trans-3,3-dimethyl-2-(1-hydrpoxy-2-hydroperoxy-2-methylpropyl)cyclopropanecarboxylate and methyl trans-3,3-dimethyl-2-formylcyclopropanecarboxylate were produced. Methyl trans-3,3-dimethyl-2-(1-hydrpoxy-2-hydroperoxy-2-methylpropyl)cyclopropanecarboxylate: LC Retention time: 17.8 min., LC-MS : M$^+$=232.

$^1$H-NMR spectrum: δ 8.82 ppm, bs(—OOH).

GC and LC analysis (internal standard method) showed that the yield of methyl trans-3,3-dimethyl-2-(1-hydrpoxy-2-hydroperoxy-2-methylpropyl)cyclopropanecarboxylate was 52.6% and that of methyl trans-3,3-dimethyl-2-formylcyclopropanecarboxylate was 5%.

The toluene solution (167 g) was subjected to a decomposition reaction as below.

Into a 500 mL flask equipped with a magnetic rotor and a reflux condenser were charged 500 mg of vanadium pentoxide and 100 g of toluene, and the toluene solution obtained above was dropwise added thereto at 60° C. over 2 hours and kept at the temperature for 1 hour. The obtained solution was were analyzed by LC to show that disappearance of the peak of methyl trans-3,3-dimethyl-2-(1-hydrpoxy-2-hydroperoxy-2-methylpropyl) cyclopropanecarboxylate in chromatogram and a peak of methyl trans-3,3-dimethyl-2-formylcyclopropanecarboxylate was detected. Yield of methyl trans-3,3-dimethyl-2-formylcyclopropanecarboxylate was 54.5%.

Example 42

Into a 100 mL flask equipped with a magnetic rotor and a reflux condenser were charged 400 mg of tungsten metal powder and 3 g of water, and 3 g of a 60 wt % aqueous hydrogen peroxide were added thereto at 40° C. over 1 hour under stirring, and reacted for 1 hour at the same temperature under stirring to produce a clear homogeneous solution. The solution was cooled to room temperature and 15 g of t-butanol and 5.3 g of anhydrous magnesium sulfate were added thereto and stirred for 1 hour at room temperature. To the obtained slurry solution was dropwise added a mixed solution of 4 g of methyl trans-3,3-dimethyl-2-(2-methyl-1-propenyl)cyclopropanecarboxylate and 8 g t-butanol over 20 minutes and reacted at 25° C. for 24 hours. A 50 g of 5 wt % aqueous sodium thiosulfate solution was added to the reaction mixture and stirred for 24 hours at room temperature. Then the mixture was extracted twice with 20 g of toluene to give 83.7 g of a toluene solution. The toluene solution was analyzed by GC to show that the toluene solution contains methyl trans-3,3-dimethyl-2-(1,2-dihydrpoxy-2-methylpropyl)cyclopropanecarboxylate, the yield of which was 80.0 %(internal standard method).

The basic foreign Applications filed on Aug. 11, 2000, No.2000-244277, filed on Oct. 27, 2000, No.2000-328816, filed on Oct. 27, 2000, No.2000-328812, filed on Nov. 6, 2000, No.2000-337152, filed on Nov. 6, 2000, No.2000-337151, and filed on Nov. 6, 2000, No.2000-337150 in Japan are hereby incorporated by reference.

What is claimed is:

1. A method for producing a hydroxy adduct compound by addition reaction of an olefinic double bond of an olefin compound, which comprises
reacting an olefin compound with hydrogen peroxide, utilizing as a catalyst at least one member selected from
(a) tungsten,
(b) molybdenum, or
(c) a tungsten or molybdenum metal compound comprising
(ia) tungsten or (ib) molybdenum and
(ii) an element of Group IIIb, IVb, Vb or VIb excluding oxygen, wherein the olefin compound is a compound of formula (I),

$$R_1R_2C=CR_3R_4 \qquad (I),$$

wherein $R_1$, $R_2$, $R_3$ and $R_4$ are the same or different and represent a hydrogen atom or an organic residue, and two geminal groups or two groups which are in syn position among the $R_1$, $R_2$, $R_3$ and $R_4$ groups may form a divalent organic residue, provided that $R_1$ to $R_4$ do not simultaneously represent a hydrogen atom, and the hydroxy adduct compound is a compound of formula (III):

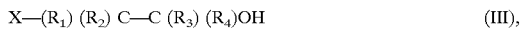

$$X\text{—}(R_1)(R_2)C\text{—}C(R_3)(R_4)OH \qquad (III),$$

wherein X represents a hydroperoxide group, and wherein the olefin compound of formula (I) is reacted with hydrogen peroxide at 0 to 45° C. in the presence of an organic solvent, to produce the hydroxy adduct compound of formula (III).

2. A method for producing a carbonyl compound by an oxidative cleavage of an olefin compound, which comprises
reacting an olefin compound with hydrogen peroxide, utilizing as a catalyst at least one member selected from
(a) tungsten,
(d) molybdenum, or
(e) a tungsten or molybdenum metal compound comprising
(ia) tungsten or (ib) molybdenum and
(ii) an element of Group IIIb, IVb, or Vb, wherein the olefin compound is a compound of formula (I),

$$R_1R_2C=CR_3R_4 \qquad (I),$$

wherein $R_1$, $R_2$, $R_3$ and $R_4$ are the same or different and represent a hydrogen atom or an organic residue, and two geminal groups or two groups which are in syn position among the $R_1$, $R_2$, $R_3$ and $R_4$ groups may form a divalent organic residue, provided that $R_1$ to $R_4$ do not simultaneously represent a hydrogen atom, and the carbonyl compound is a compound of formula (II):

$$R_aR_bC=O \qquad (II),$$

wherein a and b respectively represent 1 and 2, or 3 and 4, or $R_b$ represents a hydroxy group, and wherein 1) the olefin compound of formula (I) wherein $R_1$ to $R_4$ independently represent an organic residue is reacted with hydrogen peroxide at 30 to 100° C., to produce the carbonyl compound of formula (II) wherein $R_a$ and $R_b$ respectively represent $R_1$ and $R_2$; or 2) the olefin compound of formula (I) wherein at least one of $R_1$ to $R_4$ groups represent a hydrogen atom, is reacted with hydrogen peroxide in the presence of an organic solvent at 30 to 65° C. to produce a carbonyl compound of formula (II) wherein $R_b$ represents a hydrogen atom; or the olefin compound is reacted with aqueous hydrogen peroxide at 65 to 100° C. to produce the carbonyl compound of formula (II) wherein $R_b$ is a hydroxy group.

3. The method according to claim 1 or claim 2, wherein the reacting of the olefin compound with hydrogen peroxide is conducted in the presence of a catalyst composition obtained by reacting an aqueous hydrogen peroxide with the tungsten, molybdenum or the metal compound thereof.

4. The method according to claim 1 or 2, wherein the hydrogen peroxide is an aqueous hydrogen peroxide.

5. A method according to claim 1, which further comprises the step of decomposing a hydroxy adduct compound of formula (IIIa):

$$X\text{—}(R_1)(R_2)C\text{—}C(R_3)(R_4)OH \qquad (IIIa)$$

wherein X is a hydroperoxide group, and $R_1$ to $R_4$ represent a hydrogen atom, an organic residue or the geminal groups or two of the $R_1$ to $R_4$ groups in a syn position may form a divalent organic residue, with a catalyst selected from a metal compound of Group Va, VIII, Ib, IIb, IIIb, IVb, Vb or lanthanide, or heating to produce a carbonyl compound of formula (IV):

$$R_1R_2C=O \qquad (IV), \text{ and}$$

of formula (IVa):

$$R_3R_4C=O \qquad (IVa)$$

wherein $R_1$ to $R_4$ are as defined in connection with formula (IIIa).

6. The method according to claim 5, wherein $R_1$ and $R_2$ represent a methyl group, $R_3$ represents a hydrogen atom, and $R_4$ represents a group of formula:

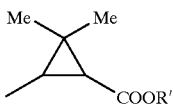

wherein R' represents an alkyl, aryl or aralkyl group.

7. The method according to claim 5, wherein the hydroxy adduct compound is a compound of formula:

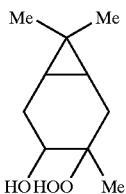

and the carbonyl compound is a compound of formula:

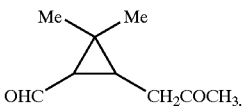

8. A method for producing a hydroxy adduct compound of formula (IIIb):

$$X—(R_1)(R_2)C—C(R_3)(R_4)OH \qquad (IIIb)$$

wherein X is a hydroxy group and $R_1$ to $R_4$ independently represent a hydrogen atom or an organic residue, which comprises reacting a hydroxy adduct compound of formula (IIIa):

$$X—(R_1)(R_2)C—C(R_3)(R_4)OH \qquad (IIIa)$$

wherein X is a hydroperoxide group, and $R_1$ to $R_4$ are the same as defined above, with a reducing agent.

9. The method according to claim 8, wherein the reducing agent is sodium thiosulfate, dimethylsulfide or triphenylphosphine.

10. The method according to claim 8, wherein $R_1$ and $R_2$ represent a methyl group, $R_3$ represents a hydrogen atom, and $R_4$ represents a group of formula:

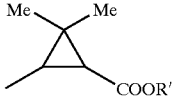

wherein R' represents an alkyl, aryl or aralkyl group.

11. The method according to claim 8, wherein $R_1$ represents a methyl group, $R_3$ represent a hydrogen atom, and $R_2$ and $R_4$ form a group of formula:

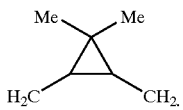

12. A hydroxy adduct compound of formula (III):

$$X—(R_1)(R_2)C—C(R_3)(R_4)OH \qquad (III)$$

wherein X is a hydroperoxide group, $R_1$ and $R_2$ represent a methyl group, $R_3$ represents a hydrogen atom, and $R_4$ represents a group of formula:

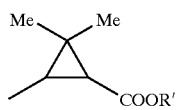

wherein R' represents an alkyl, aryl or aralkyl group.

13. A hydroxy adduct compound of formula (III):

$$X(R_1)(R_2)C—C(R_3)(R_4)OH \qquad (III)$$

wherein X is a hydroperoxide group, $R_1$ represents a methyl group, $R_3$ represents a hydrogen atom, and $R_2$ and $R_4$ form a group of formula:

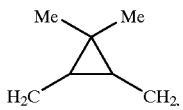

14. The method according to claim 2, wherein the olefin compound is cyclohexene and the carbonyl compound is adipic acid.

15. The method according to claim 2, wherein the olefin compound is cyclohexene and the carbonyl compound is adipoaldehyde.

16. The method according to claim 3, wherein the catalyst composition is a recovered catalyst composition for reuse.

* * * * *

UNITED STATES PATENT AND TRADEMARK OFFICE
CERTIFICATE OF CORRECTION

PATENT NO.   : 6,703,528 B2
DATED        : March 9, 2004
INVENTOR(S)  : Hagiya et al.

It is certified that error appears in the above-identified patent and that said Letters Patent is hereby corrected as shown below:

Column 27,
Lines 15-20, the second formula should read:

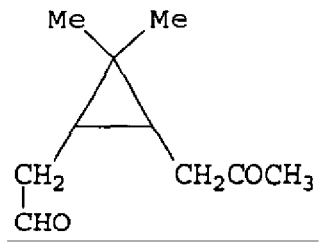

Signed and Sealed this

Eighth Day of February, 2005

JON W. DUDAS
*Director of the United States Patent and Trademark Office*